United States Patent [19]

Hori et al.

[11] Patent Number: 4,670,585
[45] Date of Patent: Jun. 2, 1987

[54] PROCESS FOR PREPARING 2-CARBOXYDIBENZOYLMETHANES

[75] Inventors: Kimihiko Hori, Utsunomiya; Koichi Nakamura, Ichikai; Naotake Takaishi, Utsunomiya, all of Japan

[73] Assignee: Kao Corporation, Tokyo, Japan

[21] Appl. No.: 898,714

[22] Filed: Aug. 21, 1986

[30] Foreign Application Priority Data

Sep. 10, 1985 [JP] Japan .................................. 60-200079

[51] Int. Cl.$^4$ ............................................. C07C 59/84
[52] U.S. Cl. ...................................... 562/459; 562/463
[58] Field of Search .............................. 562/459, 463

[56] References Cited

U.S. PATENT DOCUMENTS 3,832,362  8/1974  Leimgruber et al. ................ 562/459

FOREIGN PATENT DOCUMENTS

EP154928  9/1985  European Pat. Off. .

OTHER PUBLICATIONS

Kateka, G. F., Phytochemistry, 15(10), 1421–14, 1976.
Brown, B. T. et al., Pestic. Sci., 4(4), 473–84, 1973.

*Primary Examiner*—Paul J. Killos

*Attorney, Agent, or Firm*—Oblon, Fisher, Spivak, McClelland & Maier

[57] ABSTRACT

2-Carboxydibenzoylmethanes of the following formula

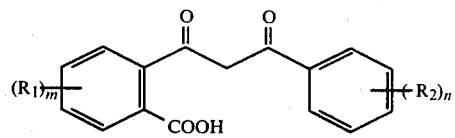

in which $R_1$ and $R_2$ are independently a substituent joined to any position of the benzene nucleus and represent a hydrogen atom, a halogen atom, a linear or branched alkyl or alkenyl group having from 1 to 18 carbon atoms, or a linear or branched, saturated or unsaturated alkoxy group having from 1 to 18 carbon atoms, m is an integer of from 1 to 4, and n is an integer of from 1 to 5 are prepared inexpensively with ease in high yield by a novel process characterized by reaction between phthalic anhydrides and acetophenones in the presence of bases.

The 2-carboxydibenzoylmethanes are useful as an inhibitor of the root geotropic response of plants or a growth regulator for plants, or a stabilizer for halogen-containing resins.

1 Claim, No Drawings

PROCESS FOR PREPARING 2-CARBOXYDIBENZOYLMETHANES

BACKGROUND OF THE INVENTION

1. Field of the Invention

This invention relates to a process for preparing 2-carboxydibenzoylmethanes and more particularly, to a process for preparing 2-carboxydibenzoylmethanes which are useful as an inhibitor of the root geotropic response in plants or a growth regulator for plants, or a stabilizer for halogen-containing resins.

2. Description of the Prior Art

2-Carboxydibenzoylmethanes have high utility as an inhibitor of the root geotropic response in plants such as a cress and ryegrass seedling and a growth regulator for plants as discussed in detail by B. T. Brown [Experientia, 28, 1290 (1972); Pesticide science, 4, 473 (1973)]. It is also known that various derivatives from starting 2-carboxydibenzoylmethanes are useful as a growth regulator for plants [DE-OS No. 2600655 (1976)].

On the other hand, 2-carboxydibenzoylmethanes are known to be useful as a stabilizer for halogen-containing resins [U.S. Pat. No. 4381360 (1983) and Japanese Laid-open Patent Application No. 56-99254].

For the preparation of these compounds, there is known a process in which phthalic diesters and acetophenones are subjected to condensation reaction in the presence of bases.

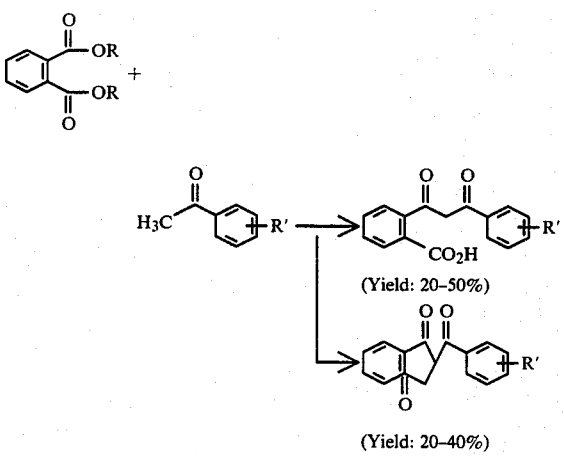

However, the above process is disadvantageous in that 2-acylindane-1,3-dione is produced as by-product at a yield of 20 to 40% and the yields of the intended 2-carboxydibenzoylmethanes are as low as 20 to 50%.

SUMMARY OF THE INVENTION

Under these circumstances in the art, the present inventors made intensive studies and, as a result, found a process of preparing 2-carboxydibenzoylmethanes in high yield, in a easy and economical manner and in large amounts. The present invention has been accomplished based on the above finding.

The process of the invention proceeds according to the following reaction formulae

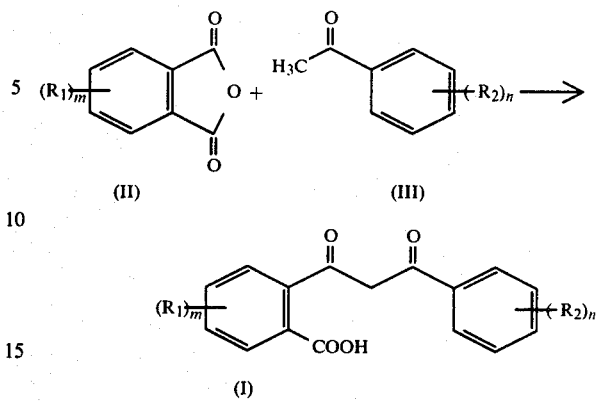

in which $R_1$ and $R_2$ are independently a substituent joined to an arbitrary position of the benzene nucleus and, respectively, represent a hydrogen atom, a halogen, atom, a linear or branched alkyl or alkenyl group having from 1 to 18 carbon atoms or a linear or branched, saturated or unsaturated alkoxy group having from 1 to 18 carbon atoms, m is an integer of from 1 to 4 and n is integer of from 1 to 5.

The present invention provides a process of preparing 2-carboxydibenzoylmethanes (I) by the reaction of phthalic anhydrides (II) and acetophenones (III) in the presence of bases.

DETAILED DESCRIPTION OF THE INVENTION AND PREFERRED EMBODIMENTS

In order to carry out the process of the invention, an acetophenone (III) and a base are dissolved in a solvent inert to the reaction, e.g. toluene, xylene or the like, at a temperature of from 0° to 200° C., preferably from 80° to 150° C. to obtain an enolate of the acetophenone. The bases include, for example, sodium hydride, sodium alcoholate, sodium amide and the like, but may be any bases capable of forming enolates. The base is added in an amount of from 1 to 20 equivalents, preferably from 1 to 6 equivalents, with respect to the acetophenone (III).

As the enolate is formed, gases such as hydrogen, ammonia and the like and alcohol are produced. These substances are removed to outside and the reaction system is further heated under reflux to complete the reaction.

Subsequently, the reaction solution was cooled down to from 0° to 150° C., preferably from 40° to 80° C., to which a phthalic anhydride (II) is added under vigorous stirring. The phthalic anhydride (II) is added in an amount of from 0.5 to 5 equivalents, preferably from 1 to 1.5 equivalents, with respect to the acetophenone (III). The solvent is distilled off from the reaction solution to obtain a slurry, to which an organic solvent capable of uniformly dissolving the intended compound (I) and an aqueous acid solution are added so that the organic phase is rendered acidic. Preferable examples of the organic solvents include methyl ethyl ketone, ethyl acetate and the like. Preferable examples of the acids include inorganic acids such as hydrochloric acid, sulfuric acid and the like, and organic acids such as succinic acid, and of these, inorganic acids are most preferred in view of isolation and purification of the final product. After collection of the organic phase, it is washed with water to an extent of pH of from 5 to 6. Thereafter, the solvent is distilled off to obtain an intended 2-carboxydibenzoylmethane (I) in a high yield.

According to the invention, 2-carboxydibenzoylmethanes (I) can be obtained inexpensively with ease in high yield.

The invention is described by way of examples.

EXAMPLE 1

700 ml of azeotropically dehydrated xylene and 99.2 g (0.51 mol) of sodium methylate (28% methanol solution) were placed in a 1 liter flask equipped with a reflux condenser, followed by heating to 110° C. to remove the methanol by distillation. To the solution, 30 g (0.2 mol) of molten p-methoxyacetophenone was added and further heated to 110° C. to distill off the methanol. When the distillation of the methanol was stopped, heating was continued at a temperature at which the solvent was refluxed, thereby completing the reaction. The reaction system was cooled down to 60° C., to which 35 g (0.24 mol) of phthalic anhydride was added under vigorous stirring. The reaction took place exothermically. As the reaction proceeded, a salt was allowed to precipitate and the reaction solution was slurried. After completion of the reaction, the xylene was distilled off and 700 ml of methyl ethyl ketone and 160 g of a 12% aqueous hydrochloric acid solution were added to the slurry with stirring to completely dissolve the solid matters. The organic phase was collected and washed three times with each 100 ml of ion-exchanged water, followed by removing the solvent by distillation under reduced pressure to obtain a yellow solid material. This material was dissolved in 200 ml of hot ethanol and cooled down to room temperature to obtain 52.1 g of intended 4'-methoxy-2-carboxydibenzoylmethane as fine yellow crystals (yield 87%).

Melting point: 156°–158° C.

IR (KBr cm$^{-1}$): 2950, 1690, 1590, 1500, 1460, 1440, 1415, 1290, 1255, 1225, 1175, 1020, 930, 850, 805, 775.

NMR (CD$_3$OD) $\delta$ppm: 3.85 (s, 3H, —OCH$_3$); 6.90–7.07 (m, 2H, proton of aromatic ring); 7.53–8.04 (m, 6H, proton of aromatic ring).

EXAMPLE 2

The general procedure of Example 1 was repeated except that 24.0 g (0.2 mol) of acetophenone was used instead of 30 g (0.2 mol) of p-methoxyacetophenone, thereby obtaining 45.6 g of 2-carboxydibenzoylmethane (yield 85%).

Melting point: 110°–112° C. (111°–113° C., in literature).

EXAMPLE 3

The general procedure of Example 1 was repeated except that 37.8 g (0.2 mol) of 3,4-dichloroacetophenone was used instead of 30 g (0.2 mol) of p-methoxyacetophenone, thereby obtaining 53.9 g of 3',4'-dichloro-2-carboxydibenzoylmethane (yield 80%).

Melting point: 170°–171° C. (170°–172° C., in literature).

EXAMPLE 4

The general procedure of Example 1 was repeated except that 32.4 g (0.2 mol) of 2,4,6-trimethylacetophenone was used instead of 30 g (0.2 mol) of p-methoxyacetophenone, thereby obtaining 44.1 g of 2',4',6'-trimethyl-2-carboxydibenzoylmethane (yield 71%).

Melting point: 154°–156° C. (155°–157° C., in literature).

What is claimed is:

1. A process for preparing 2-carboxydibenzoylmethanes of the following formula (I)

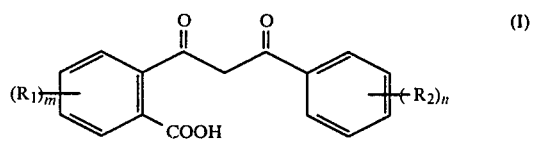

in which R$_1$ and R$_2$ are independently a substituent joined to any position of the benzene nucleus and represent a hydrogen atom, a halogen atom, a linear or branched alkyl or alkenyl group having from 1 to 18 carbon atoms, or a linear or branched, saturated or unsaturated alkoxy group having from 1 to 18 carbon atoms, m is an integer of from 1 to 4, and n is an integer of from 1 to 5, characterized by reaction between phthalic anhydrides of the general formula (II)

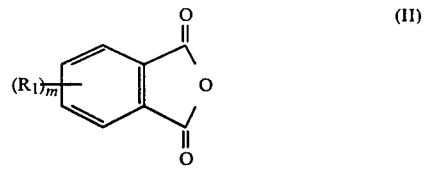

in which R$_1$ and m have, respectively, the same meanings as defined above and acetophenones of the general formula (III)

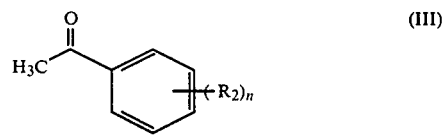

in which R$_2$ and n have, respective the same meanings as defined above.

* * * * *